United States Patent [19]

Bopp

[11] Patent Number: 6,130,353
[45] Date of Patent: Oct. 10, 2000

[54] CHIRAL SEPARATIONS OF AMINO ACIDS

[75] Inventor: Ronald J. Bopp, Downingtown, Pa.

[73] Assignee: Chiral Technologies, Inc., Exton, Pa.

[21] Appl. No.: 09/380,849

[22] PCT Filed: Mar. 18, 1998

[86] PCT No.: PCT/US98/05366

§ 371 Date: Dec. 13, 1999

§ 102(e) Date: Dec. 13, 1999

[87] PCT Pub. No.: WO98/41489

PCT Pub. Date: Sep. 24, 1998

Related U.S. Application Data

[60] Provisional application No. 60/040,987, Mar. 18, 1997.

[51] Int. Cl.[7] .................................................. C07B 55/00
[52] U.S. Cl. ................................................................ 562/401
[58] Field of Search ............................................. 562/401

[56] References Cited

U.S. PATENT DOCUMENTS 4,766,250  8/1988  Miruiss .

OTHER PUBLICATIONS

Chem Abst vol. 128 (217606 1998.

*Primary Examiner*—Paul J. Killos
*Attorney, Agent, or Firm*—Mathews, Collins, Shepard & Gould, P.A.

[57] ABSTRACT

An enantiomeric mixture of a chiral amino acid is separated into its respective enantiomers through chromatography on a chiral polysaccharide stationary phase eluting with a mobile phase comprising (i) a liquid lower alkanol and (ii) a carboxylic acid soluble in the lower alkanol. The mobile phase may also contain a liquid hydrocarbon.

16 Claims, No Drawings

CHIRAL SEPARATIONS OF AMINO ACIDS

This application claims benefit of provisional application No. 60/040,987, filed Mar. 18, 1997.

The present invention relates to the separation of chiral materials utilizing high performance liquid chromatography (HPLC) techniques.

It is know that the addition of an acidic modifier such as trifluoroacetic acid (TFA) to the mobile phase is required for the separation of certain carboxylic acids. It also is know that molecules which contain an amino group may require the addition of triethylamine (TEA) and/or diethylamine (DEA) as modifiers in order to obtain satisfactory resolution and peak shape. DEA or TEA acts as competitors with the basic analyte toward the basic silane groups on the silica support.

Tang, J Chirality, (1996) reports on the use of TFA as a mobile phase modifier for the separation of basic compounds.

DETAILED DESCRIPTION

The present invention pertains to a method of separating an enantiomeric mixture of a chiral compound containing an amino nitrogen atom, or a salt thereof, specifically an amino acid, into its respective enantiomers. This method comprises subjecting the chiral mixture to chromatography on chiral polysaccharide stationary phase. The stationary phase is then eluted with a mobile phase comprising (i) a liquid hydrocarbon, (ii) a liquid lower alkanol, and (iii) a carboxylic acid soluble in the liquid hydrocarbon and lower alkanol.

The enantiomeric HPLC separations encompassed by the present invention utilize chiral polysaccharides as stationary phases. Typically these are aromatic carbamate or ester derivatives of cellulose or amylose which can be generically represented by the formula:

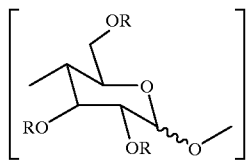

in which the depicted glucosidic linkage is either α (amylose) or β (cellulose).

The depicted R groups can be for example a phenylcarbamate or α-phenethylcarbamate, which itself is chiral, or a benzoate group. Typical R groups thus include 3,5-dimethylphenyl carbamate, α-phenethylcarbamate, and 4-methylbenzoate, e.g.:

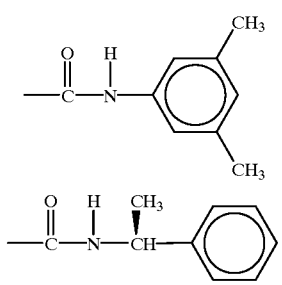

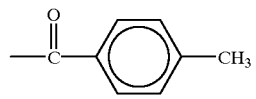

Such chiral polysaccharide stationary supports are commercially available from Chiral Technologies, Inc., Exton, Pa., under the trademarks CHIRALPAK® amylosic stationary phase and CHIRALCEL® cellulosic stationary phase. Suitable materials include CHIRALPAK® AD™, an amylose derivative in which each glucose monomer carries three 3,5-dimethylphenyl carbamate groups, CHIRALPAK® AS™, an amylose derivative in which each glucose monomer carries three (S)-α-phenethylcarbamate groups, CHIRALCEL® OD™, a cellulose derivative in which each glucose monomer carries three 3,5-dimethylphenyl carbamate groups, and CHIRALCEL® OJ™, a cellulose derivative in which each glucose monomer carries three 4-methylbenzoyl groups. Reference may be made to U.S. Pat. Nos. 4,912,205 and 5,434,299 for further details, the disclosures of which are incorporated herein by reference. Amylose derivatives, particularly CHIRALPAK® AD™, are preferred.

The stationary phase conveniently can be packed in columns adapted for use with commercially available HPLC systems, as for example those available from Shimadzu, Columbia, Md., and Jasco, Easton, Md. Generally the particle diameter will be from about 1 to about 100 μm, typically from about 5 to about 75 μm. Multiple or single columns can be employed. A simulated moving bed apparatus also can be employed, as described for example in U.S. Pat. Nos. 5,434,298, 5,434,299, 5,456,825, and 5,498,752, the disclosures of which are incorporated herein by reference.

The eluent or mobile phase comprises (i) a liquid lower alkanol, and (ii) a strong carboxylic acid soluble in the lower alkanol. The lower alkanol can contain from 1 to 6 carbon atoms such as methanol, ethanol, n-propanol, isopropanol, butanol, and the like, but preferable is ethanol or methanol. In some instances separation is poor with isopropanol but is satisfactory when the mobile phase employs ethanol or methanol.

In addition to the lower alkanol and a strong carboxylic acid, the eluent or mobile phase can contain a liquid hydrocarbon, as for example pentane, hexane, or heptane.

Gradient mixtures often will be employed; e.g., starting with a predominantly hydrocarbon mixture {such as 70:30 hydrocarbon:alkanol (v/v)} and progressively increasing the amount of alkanol to as high as 100% alkanol. The carboxylic acid can be any relatively strong acid which is soluble in the lower alkanol (and any liquid hydrocarbon which is present), as for example formic acid, acetic acid, a substituted acetic acid, propionic acid, and the like. Particularly preferred are trihaloacetic acids such as trifluoroacetic acid and trichloroacetic acid.

Without wishing to be bound by any theory of operation, it appears one of the enantiomers is retained at about the same retention whether or not the carboxylic acid is present, while the other enantiomer shows a significant increase in retention times when the carboxylic acid is present, thereby facilitating separation. It further appears the that at low pH, the amine group is protonated by the carboxylic acid with the analytes separating as ion pairs.

In one embodiment, the mobile phase also will contain a secondary or tertiary amine. This is present in less than a 1:1 molar ratio to the carboxylic acid. Preferred amines are di-(lower alkyl) amine and tri(lower alkyl)amine such as diethylamine and triethylamine. Addition of these amines to the mobile phases produces several additional benefits. The addition of certain carboxylic acids to the mobile phase can increase UV absorbance, leading to detection problems for analytes of low UV absorbance. Addition of an amine to the mobile phase, however, decreases the absorbance, thus facilitating the monitoring of the analyte elution by UV absorbance at less than 240 nm. Second, the addition of the amine can lead to significant decrease in peak tailing for basic analytes. The carboxylic acid still acts as an ion pair agent, but the amine salt complex competes with active sites on the chiral column which can cause peak tailing. This decrease in peak tailing can significantly improve the resolution.

The present method is suitable for separating chiral amino acids including both naturally occurring α-amino acids, such as alanine, arginine, lysine, phenylalanine, serine, valine, threonine, glutamic acid, DOPA, norleucine, leucine, norvaline and the like, as well as β-, γ-, and ω-amino acids. Amino acids normally exist as Zwitter ions in neutral solution so that both its carboxylic acid and amino group are ionized. Consequently, although these molecules are very insoluble in typical mobile phases, they can be separated on the polysaccharide phases through appropriate pH adjustment and control of the ion-pairing agent.

The process also can be used with a derivative of an amino acid such as a carbamate such as an N-tert.-butyloxycarbonyl or benzyloxycarbonyl derivative. Oxycarbonyl derivatives are useful since they tend to be more soluble than the free amine in the mobile phase. Typical of such derivatives are N-tert.-butyloxycarbonylproline, N-tert.-butyloxycarbonyltyrosine, and N-tert.-butyloxycarbonyltryptophane. An acid modifier is used in this case to keep the derivatized amino acid neutral.

The process also can be used with chiral amines which are not amino acids including aliphatic, cycloaliphatic, aromatic, and heterocyclic amines. The amine can be a primary, secondary, tertiary, or quaternary amine. Typical amines for which the present process is suitable include without limitation albuterol, metoprolol, propranolol, pindolol, and other propanol amines, methadone, 1-methyl-1-phenylethane, 2-aminobutane, 2-amino-1-butanol, 1-amino-1-phenylethane, 1-amino-1-(2-methoxy-5-fluorophenyl)ethane, 1-amino-1-phenyl-propane, 1-amino-1-(4-hydroxyphenyl)propane, 1-amino-1-(4-bromophenyl)-propane, 1-amino-1-(4-nitrophenyl)propane, 1-phenyl-2-aminopropane, 1-(3-tri-fluoromethylphenyl)-2-aminopropane, 2-aminopropanol, 1-amino-1-phenyl-butane, 1-phenyl-2-aminobutane, 1-(2,5-dimethoxy-4-methylphenyl)-2-aminobutane, 1-phenyl-3-aminobutane, 1-(4-hydroxyphenyl)-3-aminobutane, 1-amino-2-methylcyclopentane, 1-amino-3-methylcyclopentane, 1-amino-2-methylcyclohexane, aminophenols, and 1-amino-1-(2-naphthyl)ethane.

The separation will be conducted at ambient temperatures; e.g., 25–40° C. pH will vary depending upon the nature of the material being chromatographed but generally will be from about 2 to about 7. Typical flow rates are from about 0.2 mL/min. to about 25 mL/min., depending on the apparatus, column dimensions, and stationary phase.

Separation can be monitored by measuring the optical activity of the eluted material, using for example a device such as the IBZ Chiralyser® instrument (available from JM Science, Inc., Grand Island, N.Y.) which monitors the rotation of plane polarized light. The refractive index, evaporative light scattering, and UV detectors may be used as alternative monitors. The parameter selected for detection will depend on the specific material being eluted.

The following examples will serve to further typify the nature of the invention but should not be construed as limitation on the scope thereof which is defined solely by the appended claims.

EXAMPLE 1

A racemic mixture of norleucine was separated into its two enantiomers using CHIRALPAK® AD™, an amylose derivative in which each glucose monomer carries three 3,5-dimethylphenyl carbamate groups, as the stationary phase and 93:7:0.2 heptane:ethanol:trifluoroacetic acid as the mobile phase. The flow rate was 1 mL/min. and detection was measured at 225 nm.

EXAMPLE 2

A racemic mixture of leucine was separated into its two enantiomers using CHIRALPAK® AD™ as the stationary phase and 93:7:0.2 heptane:ethanol:trifluoroacetic acid as the mobile phase. The flow rate was 1 mL/min. and detection was measured at 225 nm.

EXAMPLE 3

A racemic mixture of norvaline was separated into its two enantiomers using CHIRALPAK® AD™ as the stationary phase and 93:7:0.2 heptane:ethanol:trifluoroacetic acid as the mobile phase. The flow rate was 1 mL/min. and detection was measured at 225 nm.

EXAMPLE 4

A racemic mixture of N-tert.-butyloxycarbonyltyrosine was separated into its two enantiomers using CHIRALPAK® AD™ as the stationary phase and 85:15:0.2 heptane:ethanol:trifluoroacetic acid as the mobile phase. The flow rate was 1 mL/min. and detection was measured at 240 nm.

EXAMPLE 5

A racemic mixture of N-tert.-butyloxycarbonyltryptophane was separated into its two enantiomers using CHIRALPAK® AD™ as the stationary phase and 85:15:0.2 heptane:ethanol:trifluoroacetic acid as the mobile phase. The flow rate was 1 mL/min. and detection was measured at 240 nm.

EXAMPLE 6

A racemic mixture of N-tert.-butyloxycarbonylproline was separated into its two enantiomers using CHIRALPAK® AD™ as the stationary phase and 93:7:0.2 heptane:ethanol:trifluoroacetic acid as the mobile phase. The flow rate was 1 mL/min. and detection was measured at 235 nm.

EXAMPLE 7

As note the process can be practiced with chiral amines which are not amino acids, as following illustrates. A chiral mixture of 1-(3-hydroxymethyl-4-hydroxyphenyl)-2-(tert.-butylamino)-ethan-1-ol was chromatographed on a stationary phase of CHIRALCEL® OJ™, a cellulose derivative in which each glucose monomer carries three 4-methylbenzoyl groups, at room temperature at a flow rate of 1 mL/min., utilizing 93:7:0.1 hexane:ethanol:diethylamine as the mobile phase. Separation was measured by absorption at 230 nm. Only a single peak was observed. When 95.5:4.5:0.1:0.17 hexane:ethanol:trifluoroacetic acid:triethylamine was utilizing as the mobile phase, separation into two distinct peaks was observed.

EXAMPLE 8

1-(Naphth-1-yloxy)-3-(isopropylamino)-propan-2-ol was separated into its two enantiomers using CHIRALCEL® OD™, a cellulose derivative in which each glucose monomer carries three 3,5-dimethylphenyl carbamate groups, as the stationary phase and 80:20:0.2:0.34 hexane:ethanol:trifluoroacetic acid:triethylamine as the mobile phase.

EXAMPLE 9

Following the procedure of example 8, 1-[4-(2-methoxyethyl) phenoxy]-3-(isopropylamino)-propan-2-ol was separated into its two enantiomers using CHIRALCEL® OD™ as the stationary phase and 80:20:0.2:0.34 hexane:ethanol:trifluoroacetic acid:triethylamine as the mobile phase

What is claimed is:

1. The method of separating an enantiomeric mixture of a chiral amino acid, or a salt or derivative thereof, into the respective enantiomers which comprises subjecting said mixture to chromatography on chiral polysaccharide stationary phase eluting with a mobile phase comprising (i) a liquid lower alkanol and (ii) a carboxylic acid soluble in the liquid hydrocarbon and lower alkanol.

2. The method of claim 1 wherein said carboxylic acid is acetic acid or a substituted acetic acid.

3. The method of claim 2 wherein said carboxylic acid is a trihaloacetic acid.

4. The method of claim 3 wherein said trihaloacetic acid is trifluoroacetic acid.

5. The method of claim 1 wherein said lower alkanol is ethanol.

6. The method of claim 1 wherein said lower alkanol is methanol.

7. The method of claim 1 wherein said mobile phase comprises a tertiary amine.

8. The method of claim 7 wherein said tertiary amine is tri-(lower alkyl) amine.

9. The method of claim 8 wherein said tertiary amine is triethylamine.

10. The method of claim 1 wherein said chiral polysaccharide stationary phase is an amylose derivative.

11. The method of claim 10 wherein in which each glucose monomer of said amylose derivative carries three 3,5-dimethylphenyl carbamate groups.

12. The method of claim 1 wherein said amino acid derivative is a carbamate derivative.

13. The method of claim 12 wherein said carbamate derivative is a N-tert.-butyloxycarbonyl derivative.

14. The method of claim 1 wherein said mobile phase also contains a liquid hydrocarbon.

15. The method of claim 14 wherein said hydrocarbon is pentane, hexane, or heptane.

16. The method of separating a mixture of a chiral amino acid, or a salt or derivative thereof, into the respective enantiomers which comprises subjecting said mixture to chromatography on chiral polysaccharide stationary phase with a mobile phase comprising (i) a liquid hydrocarbon, (ii) ethanol, and (iii) a trifluoroacetic acid.

* * * * *